United States Patent [19]

Mikola et al.

[11] Patent Number: 4,808,541

[45] Date of Patent: Feb. 28, 1989

[54] DETERMINATION METHOD UTILIZING REAGENTS COVALENTLY LABELLED WITH ESSENTIALLY NON-FLUORESCENT LANTHANIDE CHELATES IN COMBINATION WITH TIME-RESOLVED FLUORESCENCE SPECTROSCOPY AND THE REAGENTS TO BE USED IN THE METHOD

[75] Inventors: Heikki Mikola; Veli-Matti Mukkala; Ilkka Hemmilä, all of Turku, Finland

[73] Assignees: LKB Produkter AB, Bromma, Sweden; Wallac OY, Turku, Finland

[21] Appl. No.: 16,789

[22] Filed: Feb. 20, 1987

Related U.S. Application Data

[63] Continuation of Ser. No. 679,047, filed as PCT SE84/00089 on Mar. 13, 1984, published as WO84/03698 on Sep. 27, 1984, abandoned.

[30] Foreign Application Priority Data

Mar. 15, 1983 [SE] Sweden .................................. 8301395

[51] Int. Cl.$^4$ ........................................... G01N 33/566
[52] U.S. Cl. ..................................... 436/501; 436/56; 436/536; 436/537; 436/546; 436/547; 435/7
[58] Field of Search ............... 436/501, 546, 800, 547, 436/536, 537, 56, 805; 435/7; 260/502.4 R, 502.4 P, 454; 558/17; 562/443

[56] References Cited

U.S. PATENT DOCUMENTS

| | | | |
|---|---|---|---|
| 3,928,509 | 12/1975 | Diery et al. | 260/945 |
| 3,957,863 | 5/1976 | Diery et al. | 260/534 |
| 3,974,090 | 8/1976 | Mithcell . | |
| 3,994,966 | 11/1976 | Sundberg et al. | 260/518 R |
| 4,058,732 | 11/1977 | Wieder | 250/461 |
| 4,133,873 | 1/1979 | Noller | 474/8 |
| 4,144,224 | 3/1979 | Moser | 260/45.75 |
| 4,228,184 | 10/1980 | Ondetti et al. | 562/443 |
| 4,259,313 | 3/1981 | Frank | 436/800 |
| 4,293,466 | 10/1981 | Di Battista et al. | 260/45.8 |
| 4,341,957 | 7/1982 | Wieder . | |
| 4,352,751 | 10/1982 | Wieder et al. | 435/188 |
| 4,353,751 | 10/1982 | Baudouin et al. | 106/306 |
| 4,374,120 | 2/1983 | Soini et al. | 436/546 |
| 4,565,790 | 1/1986 | Hemmila et al. | 436/800 |

FOREIGN PATENT DOCUMENTS

| | | |
|---|---|---|
| 86330/82 | 1/1983 | Australia . |
| 1028347 | 3/1978 | Canada ............................ 260/501.5 |
| 850077 | 11/1982 | European Pat. Off. . |
| 0071564 | 2/1983 | European Pat. Off. . |
| 850244 | 3/1984 | European Pat. Off. . |
| 723316 | 2/1955 | United Kingdom . |
| 1363099 | 8/1974 | United Kingdom . |
| 1598610 | 9/1981 | United Kingdom . |

OTHER PUBLICATIONS

Smith et al., Ann. Clin. Biochem., 18 (1981), 253–274.
Ullman, Edwin, F., "Ligand Assay", Recent Advances in Fluorescence Immunoassay Techniques, (1981), pp. 113–135.

(List continued on next page.)

Primary Examiner—Robert J. Warden
Assistant Examiner—Stephen C. Wieder
Attorney, Agent, or Firm—Fisher, Christen & Sabol

[57] ABSTRACT

Compound having the following structure:

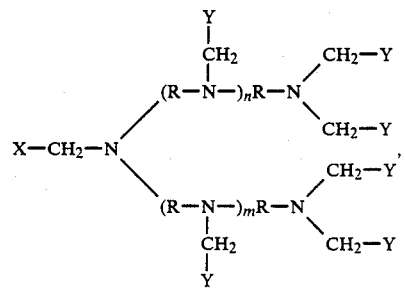

R is a direct chain or branched alkylene group comprising 2–8 carbon atoms,
n and m are 0 or 1,
Y is a carboxylic or phosphonic acid, and
X is an active functional group which permits covalent coupling to a bio-organic molecule.

8 Claims, 1 Drawing Sheet

OTHER PUBLICATIONS

Soini et al., Clin., Chem., 25, (1979), 353–361.
Hnatowich et al., Int. J. Appln. Radiat. Isot. 33, (1982), pp. 327–332.
Klopper et al., J. Nucl. Med., 13 (1972), pp. 107–110.
Halverson (1964), J. Chem., Phys. 41, 157.
Kareseva & Karesev (1975), Koord. Khim. 1, 926.
Muraveva (1977), Zh. Neorg. Khim 22, 3009.
Taketatsu (1979), Anal. Chim. Acta 108, 429.
Brittain, (1980), Inorg. Chem. 19, 640.
Makhijani et al., J. Ind. Chem. Soc, vol. 60, 1978, pp. 840–841.
Nakatani et al., Rev. Phys. Chem., Japan, vol. 42, 1972, pp. 103–107.
Moller et al., Chem. Rev., vol. 65, 1965 pp. 1, 10, 13 and 25 to 50.
Leung, Biochem. & Biophys. Res. Comm. vol. 75, No. 1, 1977, pp. 149–155.
Wieder, Chem. Abs., vol. 90, 1979 (citing Immunoflouresc. Tech. Proc. Int. Conf. 6th 1978 pp. 67080).

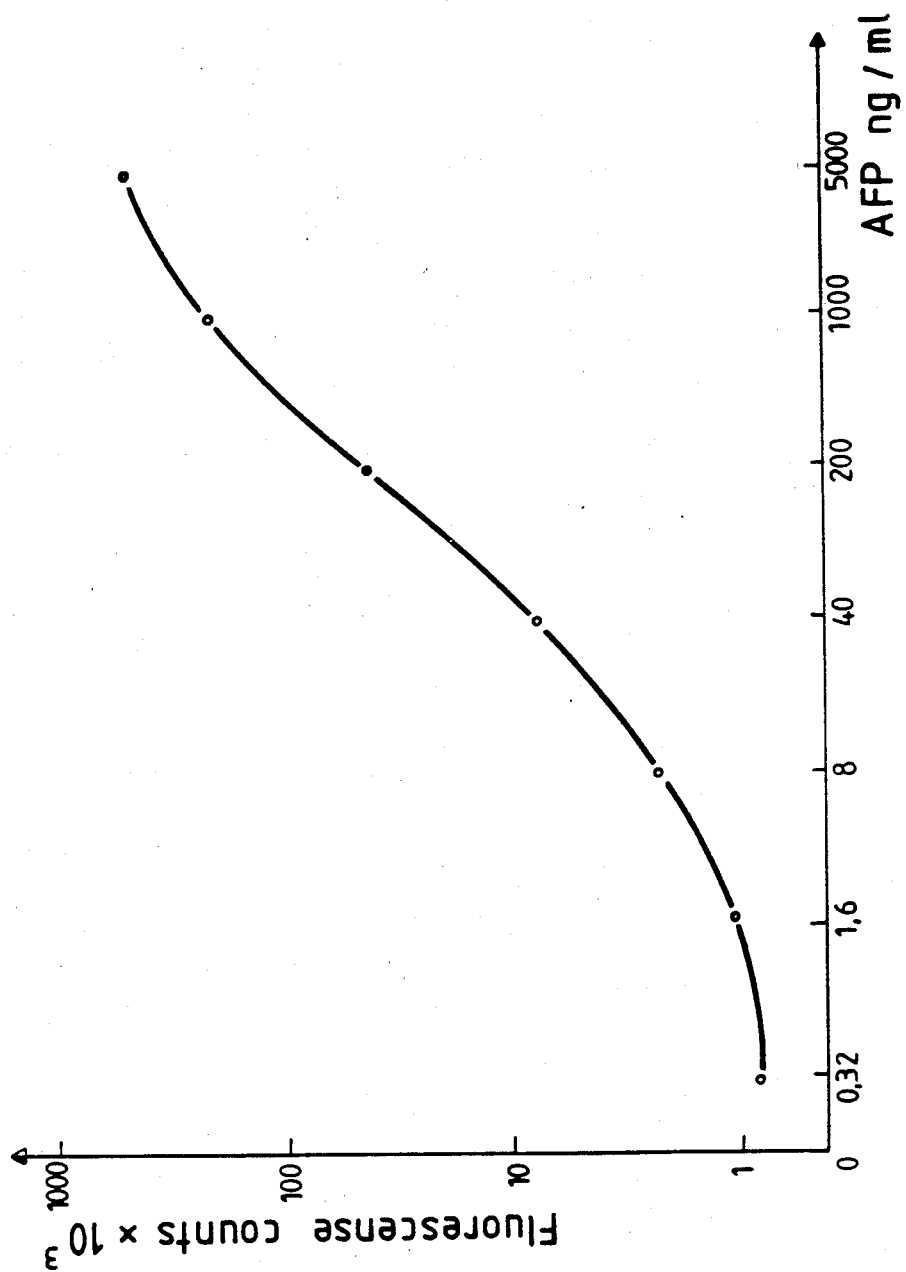

DETERMINATION METHOD UTILIZING REAGENTS COVALENTLY LABELLED WITH ESSENTIALLY NON-FLUORESCENT LANTHANIDE CHELATES IN COMBINATION WITH TIME-RESOLVED FLUORESCENCE SPECTROSCOPY AND THE REAGENTS TO BE USED IN THE METHOD

TECHNICAL FIELD

This is a continuation of application Ser. No. 679,047, filed as PCT SE 84/00089 on Mar. 13, 1984, published as WO 84/03698 on Sep. 27, 1984, abandoned.

The present invention refers to a compound.

BACKGROUND ART

Immunoassay is a field in which the sensitivity of the analysis method often is of decisive importance as the amount of analyte in different biological liquids usually is very low. As a result of this radioisotopes have been widely used as labels in immunoassays despite the disadvantages caused by their use. At the same time, however, a very intense research has been carried out with the aim of replacing the radioisotopes with labels giving at least the same or a higher sensitivity than the isotopes. Fluorescent molecules have in these connections been presented as one of the most potential alternatives to radioisotopes. Comprehensive surveys have recently been published, which give a good general view of fluoroimmunoanalytical determinations known at present (see Smith et al. (1981) Ann. Clin. Biochem. 18, 253-274, Ullman (1981) "Recent Advances in Fluorescence Immunoassay techniques").

The sensitivity of the fluorescent labels in immunoassay, in spite of the fact that it is theoretically very high, has been seriously limited by a high background fluorescence. Usually, it has been possible to reduce the background fluorescence, so that a desired sensitivity could be obtained. The above mentioned surveys also describe the limitations which have made the use of conventional fluorescent labels difficult in immunoassay of analytes which require a high sensitivity corresponding to that which can be obtained with radioisotopes.

The use of time-resolved fluorescence (see Soini et al (1979) Clin. Chem. 25, 353-361) makes it, however, possible to separate the specific fluorescence of the label from the disturbing, unspecific background fluorescence. The principle of the use of time-resolved fluorescence when following biospecific affinity reactions is described in the U.S. Pat. No. 4,374,120 and the European patent application No. 82850077.7. In time-resolved fluorescence the fluorescent label is excited by means of a light pulse of a short duration and the fluorescence is not detected until a certain period of time has elapsed from the excitation pulse. During the time which passes between excitation and detection, the fluorescence from any interfering sources will decay, so that only the signal from the label usable for time-resolved fluorescence is detected. Such a label should have as high fluorescence as possible, a relatively long emission wave-length, a large Stoke's shift and a chemical structure which makes it possible to couple the label covalently to antigens, haptens, antibodies, nucleic acids and polynucleotides. A fluorescence label, which fulfils the above mentioned requirements (U.S. Pat. No. 4,374,120) comprises a lanthanide chelate formed by a lanthanide and an aromatic $\beta$-diketone, the lanthanide being bound to antigen, hapten, antibody, nucleic acid or polynucleotide via an EDTA-analogue so that a fluorescent lanthanide complex is formed. The fluorescence decay time of the label is long, 50–1000 $\mu$sec, which makes it most suitable for the time-resolved detection principle. The fluorescence from the label can either be measured when the marker is bound to antigen, hapten, antibody, nucleic acid or polynucleotide, or the lanthanide can under suitably chosen circumstances be released from these by dissociating the bond between the lanthanide and the EDTA-analogue, the fluorescence being caused in solution in the presence of an aromtic $\beta$-diketone, a synergistic compound and a detergent which together with the lanthanide form a micellar system having a fluorescence which is characteristic of the lanthanide (European patent application No. 82850077.7).

In the use of lanthanides as labels in biospecific affinity reactions two functions can in principle be distinguished. On the other hand, the lanthanide should form a fluorescent chelate and on the other hand it should be bound to a bio-organic molecule, which is an antigen, a hapten, an antibody, a nucleic acid or a polynucleotide, in order to be usable as a label in biospecific affinity reactions.

The prerequisites for the formation of a fluorescent lanthanide chelate are described in the European patent application No. 83850244.1. A specific controlled binding of a lanthanide to a bio-organic molecule has proved to be difficult even if a number of alternative solutions has been tested. In such a binding it is desirable that the lanthanide is bound to the bio-organic molecule with a very high affinity and that the binding is kinetically stable. The primary ligand which is covalently bound to the bio-organic molecule and which also chelates the lanthanide, can also absorb the excitation energy which is then transferred to the lanthanide according to the principles which are described in the European patent application No. 83850244.1, or alternatively the primary ligand only acts as an intermediary for the binding of the lanthanide to the bio-organic molecule. The EDTA analogue mentioned earlier (U.S. Pat. No. 4,374,120) follows the latter principle. Aminophenyl-EDTA-Eu can e.g. be diazotated and thereafter be coupled to tyrosine or histidine residues in a protein. The synthesized protein-EDTA-Eu complex gives, however, upon excitation a very low lanthanide fluorescence of a long decay time, since the primary ligand does not absorb and transfer the necessary excitation energy to the lanthanide. In spite of this the ligand functions excellently in bio-specific affinity reactions according to the principles which are described in the U.S. Pat. No. 4,374,120 and the European patent application No. 82850077.7.

Ethylenediamine tetraacetic acid (EDTA) is a well known and commonly used compound, which under the suitable conditions forms stable chelates with a large number of metal ions (see Ringbom (1964) Komplek-sometrisk analys). The chelate forming characteristics of the molecule can be utilized to bind e.g. lanthanides to bio-organic molecules for use in bio-specific affinity reactions, if a covalent coupling of the ligand to the bio-organic molecule can be carried out. This has been done by e.g. synthesizing an EDTA dianhydride, which is coupled to a suitable bio-organic molecule, a diamine-triacetic acid derivative of the molecule is, then, obtained when the fourth carboxyl group is used for the conjugation (see Wieder et al, U.S. Pat. No. 4,353,751). Moreover, an aminophenyl-EDTA derivative can be synthesized which can be used to bind the EDTA structure to the bio-organic molecule (see Sundberg et al, U.S. Pat. No. 3,994,966).

There are, however, other compounds than EDTA which form stable chelates with metal ions (see Ringbom (1964) Kompleksometrisk analys). One of them, diethylenetriaminepentaacetic acid (DTPA) has e.g. been used to bind radioisotopes in connection with the examination of kidney functions (see Klopper et al. (1972) J. Nucl. Med. 13, 107-110). DTPA has also been coupled to protein by the use of a cyclic anhydride of the molecle, four carboxyl groups then remaining for chelating (see: Hnatowich et al. (1982) Int. J. Appl. Radiat. Insot. 33, 327-332).

DISCLOSURE OF INVENTION

The object of the present invention is to provide a chelating compound, which strongly chelates i.a. lanthanides, but which also comprises active functional groups which makes it possible to bind the metal chelate to a bio-organic molecule comprising e.g. hapten, antigen, nucleic acid or antibody. The characteristic features of the invention are apparent from the claims attached to the specification.

BRIEF DESCRIPTION OF DRAWING

The drawing shows a typical AFP determination with duplicate standards for seven different concentrations.

DETAILED DESCRIPTION

Compounds according to the invention can be derived starting from the following basic structure

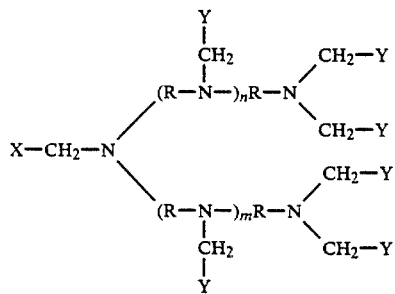

in which

R is a 2 to 8 atoms long covalent bridge comprising alkylene groups

Y comprises carboxylic or phosphonic acid and the number varies depending on n and m.

X is an active functional group which permits coupling to a bio-organic molecule and comprises e.g. an aromatic ring comprising a $NH_2$, OH, COOH or NCS group.

n and m are 0 or 1.

X can change place with one of the Y functions in the molecule.

The chelating compounds can be synthesized in the following ways:

Step 1: 2.0 g diethylenetriamine is dissolved in 25 ml toluene and 1.0 g 4-nitrobenzylbromide dissolved in 25 ml toluene is added. The reaction mixture is stirred for 3 hours at room temperature. The precipitate is filtrated and the toluene phase is extracted with water. The water phase is extracted with chloroform which is evaporated to dryness. The final product consists of a yellow syrup (0.85 g, 77% yield).

TLC: silica gel; ammonia ethanol 1:4; $R_f$ for $N^1$ compound 0.38 and for $N^2$ compound 0.29.

$^1$H-N.M.R. (CDCl$_3$): $\delta = 7.8$

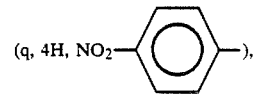

3.7 for $N^2$ and 3,9 for $N^1$ compound

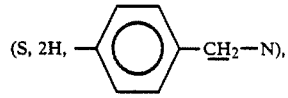

2,7 (m, 8H,—$CH_2CH_2$—)1,6 (S, 2H—NH—&—$NH_2$)
U.V. (H$_2$O): $\lambda$ max=273 nm Step 2: The mixture of $N^1$- and $N^2$-(4-nitrobenzyl)diethylenetriamine is dissolved in water. The water solution is made alkaline (pH 9-11) with 7M KOH solution and is heated during stirring to 50° C. A water solution of bromoacetic acid (2.5 g) is added slowly and pH is kept between 9-11 by means of the KOH solution. After the addition the stirring and the heating (50° C.) are continued for at least 4 hours, KOH solution being added now and then to keep pH in between 9 and 11. The reaction mixture is acidified (pH about 1), the insignificant precipitate appearing on the cooling, then being filtrated away. The solution is evaporated to a smaller volume, a salt then being precipitated, the precipitation of which is facilitated by adding acetone. The solution is evaporated to dryness and an impure raw product is obtained (3.1 g, containing about 50% of the desired compound). The product is purified by means of preparative liquid chromatography (Waters PrepPAK-500/C$_{18}$, with H$_2$0), then also the different isomers being separated from each other.

TLC: silica gel; acetonitrile/water 4:1; $R_f$ for $N^1$ compound 0.16 and for $N^2$ compound 0.33.

$^{13}$C-N.M.R. (D$_2$O): $\delta = 52.4$ & 52.6 (—$CH_2CH_2$—), 57.8 (—$CH_2COOH$) 59.9

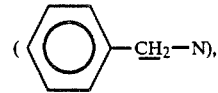

126.9, 134.3, 141.8 & 150.7

173.9 (—COOH) (for $N^2$ compound)
U.V. (H$_2$O): $\mu$ max=269 nm
I.R. (KBr): $\nu$ max=1740, 1530, 1350 cm$^{-1}$ Step 3: 2.0 g of a compound from the previous synthesis step is dissolved in 50 ml water and 0.2 g of palladium on activated carbon (5%) is added to the solution in a pressure reactor. The reactor is cooled to 0°-+5° C. and is washed with nitrogen gas and hydrogen gas. The reduction takes place at 0°-+5° C. at about 1 MPa (pressure above atmospheric). The reaction is followed on thin layer plates (acetonitrile water 4:1), by means of a liquid chromatohgraphy (HPLC) or UV-spectrophotometry. Final product 1.7 g, yield 89%.

TLC: silica gel; acetonitrile/water 4:1; $R_f$ for $N^1$ compound as $Eu^{3+}$ chelate 0.25 and $N^2$ compound 0.30.

$^{13}$C-N.M.R. (D$_2$O): $\delta$=150.9, 140.9, 121.7 & 120.0

183 (—COOH) (for $N^2$ compound as $Eu^{3+}$ chelate)

U.V. (H$_2$O): $\lambda$ max=284 & 238 nm (~1:8)

I.R. (KBr): $\nu$ max=1580–1640, 1400 cm$^{-1}$

Step 4: 2.3 g of $N^2$-(4-aminobenzyl)-diethylenetriamine-$N^1,N^1$, $N^3$, $N^3$-tetraacetic acid is dissolved in about 15 ml of water and the solution is added to a reagent mixture containing 1.7 g of thiophosgene, 15 ml of chloroform and 1 g of sodium hydrogen carbonate. The reaction mixture is strongly stirred for about 20 minutes in room temperature. The phases are separated and the water phase is washed with chloroform (3×5 ml), it then being evaporated to dryness and the obtained product is washed with ethanol. Final product 2.2 g, yield 83%.

TLC: Silica gel; acetonitrile/water 4:1; $R_f$ for $N^1$ and $N^2$ compounds 0.45

U.V. (H$_2$O): $\lambda$ max=268×280 nm (~1:1)

I.R. (KBr): $\nu$ max=2000–2200 cm$^{-1}$

Reaction scheme:

Step 1:

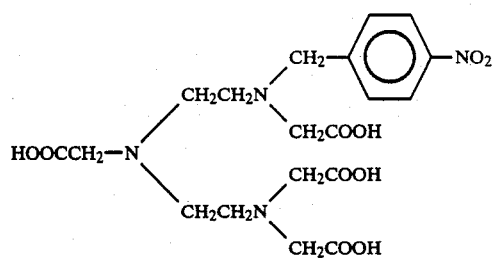

Step 2:

BrCH$_2$COOH

-continued
Reaction scheme:

(The isomers are separated by HPLC).

Step 3:

Pd/C (5%)
Corresponding aminoderivative

Step 4:

Cl$_2$C = S
Corresponding isothiocyanato derivative.

The other compounds mentioned can be synthesized in a corresponding way starting from the corresponding polyalkylene-polyamine. The carboxylic groups also be replaced by phosphonic acid (K. MOEDRITZER-R. R. IRANI, J. Org. Chem. 31, 1603 (1966). The applicability of the invention is illustrated below by means of a non-limiting example of execution.

Example 1. Determination of alphaphetoprotein (AFP). The chelating compound $N^2$-(p-isothiocyanato benzyl)-diethylenetriamine-N;hu 1, $N^1$, $N^3$, $N^3$-tetraacetic acid (p-ITC-B-DTTA) is used to chelate europium and to bind the europium chelate to a monoclonal anti-AFP antibody. The europium labelled antibody was used in the immunoassay of AFP.

LABELLING THE ANTIBODY WITH EUROPIUM p-ITC-B-DTTA-Eu was added to an anti-AFP solution (0.2 mg in 200 $\mu$l PBS) at 0° C. and the pH of the solution was adjusted to 9.5 by means of 10 $\mu$l of 1M Na$_2$CO$_3$. The molar ratio between chelate and antibody was 60:1. The reaction mixture was incubated over night, whereupon the antibody conjugate was purified from free unreacted label by means of gel filtration on a Sephadex G-50 column (Pharmacia). The degree of conjugation was determined by measuring the europium fluorescence and it was found to be about 7 Eu-/IgG.

Immunoassay

Polystyrene tubes were coated with anti-AFP by incubating the tubes over night at room temperature with 250 $\mu$l of a solution containing 1 $\mu$g of anti-AFP in 50 mM, K$_2$HPO$_4$+9 g/l of NaCl. The tube surface was saturated with 250 $\mu$l of a solution containing 0.5% of BSA in Tris-HCl buffer, pH 7.70 (2 hours at room temperature). After washing the tubes were used for the immunoassay.

25 $\mu$l serum samplesor corresponding standards were incubated for 1 hour in the coated tubes together with 50 ng of europium labelled anti-AFP which had been added in 225 $\mu$l of Tris-HCl buffer, pH 7.7 containing 0.9% NaCl, 0.05% NaN$_3$, 0.5% BSA, 0.05% bovine gammaglobuline, 0.01% Tween-40 and 20 $\mu$M DPTA.

After incubation the tubes were aspirated and washed three times with 2 ml of physiological sodium chloride solution containing 0.05% NaN₃.

Quantitation of Europium by Means of Time-Resolved Fluorescence

The amount of europium, which via the chelate and the labelled antibody has been bound in the immunometric analysis to the surface of the tube, was quantitated by adding 0.5 ml enhancement solution (15 μM β-naphthoyltrifluoroaceton,e 50 μM trioctylphosphine oxide, 0.1% of Triton X-100 in phthalateacetate-buffer pH 3.2). The solution dissociates europium from the chelate, a new florescent chelate thus being formed in the micellar phase, the amount of which is proportional to the time-resolved fluorescence signal obtained and the amount of europium released.

Result

The result from a typical AFP determination with duplicate standards for seven different concentrations is shown in Table 1 and on the attached drawing.

We claim:

1. In a method for following bio-specific affinity reactions for detecting an analyte by the use of a bio-organic molecule covalently labelled with a lanthanide chelate, said lanthanide chelate being measured by releasing the lanthanide and formation of a fluorescent lanthanide chelate that is determined by time-resolved fluorescence spectroscopy, the improvement being the use of a chelating group that has been bound covalently to said bio-organic molecule by reaction of said molecule with a compound having the structure:

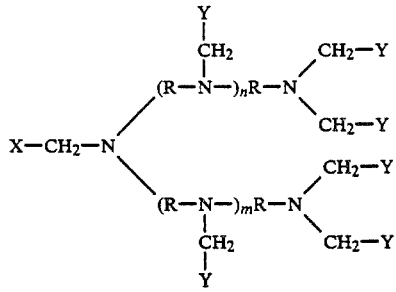

or with a lanthanide chelate thereof in which the lanthanide is the same as in the fluorescent chelate, wherein R is a straight or branched alkylene group having 2 to 8 carbon atoms; n and m are each 0 or 1; Y is a carboxylic acid group or a phosphonic acid group; and X is an active functional group which allows covalent coupling to said bio-organic molecule, with the provision that X can change place with one of the Ys.

2. In a method for following bio-specific affinity reactions for detecting an analyte by the use of a bio-organic molecule covalently labelled with a lanthanide chelate, said lanthanide chelate being measured by releasing the lanthanide and formation of a fluorescent lanthanide chelate that is determined by time-resolved fluorescence spectroscopy, the improvement being the use of a chelating group that has been bound covalently to said bio-organic molecule by reaction of said molecule with a compound having the structure:

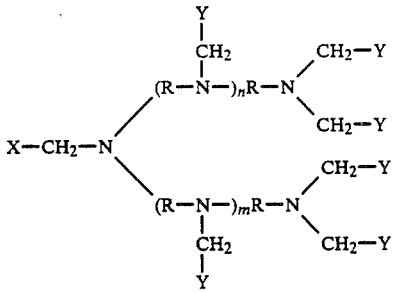

or with a lanthanide chelate thereof in which the lanthanide is the same as in the fluorescent chelate, wherein R is a straight or branched alkylene group having 2 to 8 carbon atoms; n and m are each 0 or 1; Y is a carboxylic acid group or a phosphonic acid group; and X is an alkylene group having 2 to 8 carbon atoms or a phenyl ring, each of which has a NH₂—, HO—, —COOH, isothiocyanate or isocyanate group for the binding to said bio-organic molecule, with the provision that X can change places with one of the Ys.

3. Method according to claim 2 wherein R is an ethylene group; n and m are each 0; Y is a carboxylic group; and X is either a p-aminophenyl group or a p-isothiocyanatophenyl group, with the provision that X can change places with one of the Ys.

4. Method according to claim 2 wherein said bio-organic molecule is an antibody.

5. Method according to claim 2 wherein said bio-organic molecule is an antigen or a hapten.

6. In a method for time-resolved fluoroimmunoassays employing an antibody or an antigen covalently labelled with a lanthanide chelate, said lanthanide chelate being measured by releasing the lanthanide and formation of a fluorescent lanthanide chelate that is determined by time-resolved fluorescence spectroscopy, the improvement being the use of a chelating group that has been bound to said antigen or antibody by reaction of said antibody or antigen with a compound having the structure:

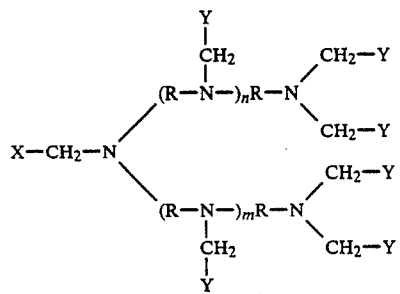

or with a lanthanide chelate thereof in which the lanthanide is the same as in the flourescent chelate, wherein R is a straight or branched alkylene group having 2 to 8 carbon atoms; n and m are each 0 or 1; Y is a carboxylic acid group or a phosphonic acid group; and X is an active functional group which allows covalent coupling to said antibody or antigen, with the provision that X can change place with one of the Ys.

7. In a method for time-resolved fluoroimmunoassays employing an antibody or an antigen covalently labelled with a lanthanide chelate, said lanthanide chelate being measured by releasing the lanthanide and formation of a fluorescent lanthanide chelate that is determined by time-resolved fluorescence spectroscopy, the improvement being the use of a chelating group that has been bound to the said antigen or antibody by reaction of said antibody or antigen with a compound having the structure:

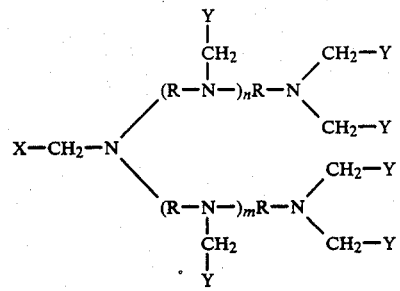

or with a lanthanide chelate thereof in which the lanthanide is the same as in the fluorescent chelate, wherein R is a straight or branched alkylene group having 2 to 8 carbon atoms, n and m are each 0 or 1; Y is a carboxylic acid group or a phosphonic acid group; and X is an alkylene group having 2 to 8 carbon atoms or a phenyl ring, each of which has a $NH_2$—, HO—, —COOH, isothiocyanate or isocyanate group for the binding to said antibody or antigen, with the provision that X can change places with one of the Ys.

8. Method according to claim 7 wherein R is an ethylene group; n and m are each 0, Y is a carboxylic group; and X is either a p-aminophenyl group of a p-isothiocyanatophenyl group.

* * * * *